US006991635B2

(12) United States Patent
Takamoto et al.

(10) Patent No.: US 6,991,635 B2
(45) Date of Patent: Jan. 31, 2006

(54) INTRACARDIAC SUTURE DEVICE

(75) Inventors: Shinichi Takamoto, Tokyo-to (JP);
Yoshihiro Suematsu, Tokyo-to (JP);
Katsuya Miyagawa, Osaka (JP);
Yoshikazu Kishigami, Osaka (JP)

(73) Assignee: Nipro Corporation, Osaka-Fu (JP)

( * ) Notice: Subject to any disclaimer, the term of this patent is extended or adjusted under 35 U.S.C. 154(b) by 618 days.

(21) Appl. No.: 10/260,435

(22) Filed: Oct. 1, 2002

(65) Prior Publication Data
US 2003/0065338 A1 Apr. 3, 2003

(30) Foreign Application Priority Data
Oct. 1, 2001 (JP) .............................. 2001-305667

(51) Int. Cl.
*A61B 17/04* (2006.01)

(52) U.S. Cl. ..................... 606/144; 606/139; 606/148

(58) Field of Classification Search ................ 606/139, 606/144, 145, 147, 148

See application file for complete search history.

(56) References Cited

U.S. PATENT DOCUMENTS 5,792,153 A * 8/1998 Swain et al. ................ 606/144
6,454,777 B1 * 9/2002 Green ........................ 606/144
6,551,330 B1 * 4/2003 Bain et al. .................. 606/144

* cited by examiner

Primary Examiner—Anhtuan T. Nguyen
Assistant Examiner—Robert Lynch
(74) Attorney, Agent, or Firm—Birch, Stewart, Kolasch & Birch, LLP

(57) ABSTRACT

An intracardiac suture device comprises: a first shaft assembly 1 including a first shaft 11 and a first suture needle-holding means 4 provided at a distal end of the first shaft 11; a second shaft assembly 2 comprising a second shaft 21; a third shaft assembly 3 comprising a third shaft 31 and a handling portion 33; and a puncture assembly 5 provided at a proximal end thereof with a second suture needle-holding means 51. The second shaft 21 is protrusible by sliding-movement from the distal end of the first shaft 11 toward the first suture needle-holding means 4, and a suture needle 6 is transferable between the first suture needle-holding means 4 and the second suture needle-holding means 51 when the third shaft 31 is slid to the distal end of the second shaft 21 after sliding the second shaft 21 to a position where a suture site is held between the second shaft 21 and the first suture needle-holding means 4.

9 Claims, 11 Drawing Sheets

INTRACARDIAC SUTURE DEVICE

BACKGROUND OF THE INVENTION

The present invention relates to an intracardiac suture device for use in treatment of intracardiac defects by suturing the defective portion with a suture needle.

For treatments of intracardiac defects such as atrial septal defect, ventricular septal defect and valvular disease, it is general practice to perform surgical operations with an artificial heart-lung machine (i.e., an extracorporeal circulation system). The heart-lung machine is a device, which performs hemoperfusion instead of the heart of a patient during the stopped of the pumping action of the heart and acts the breathing function for the lung by prosecution of the gas exchange in the blood. The heart-lung machine generally comprises four main components, i.e., a blood pump, an oxygenator, a heat exchanger and a reservoir. The heart-lung machines have been used widely as auxiliary measures for extracorporeal circulation in open heart surgery. Further, they have also been used as auxiliary measures for supplementary circulation when any bad circulation of the internal organ and/or organization arises from considerable decrease in the pumping action of the heart, or auxiliary measures for gas exchange when the function of the patient's lung is considerably damaged. In addition, the lung-heart machines are used in membrane oxygenator-assisted extracorporeal circulation (ECMO), and as auxiliary measures for extracorporeal circulation in thoracic aortic aneurysm surgery.

In the first era of cardiac surgery, surgical operations of pulsating hearts have been carried out blindly by the feel and thus the safety has come up as a serious problem before development of an artificial heart-lung machine. In 1953, Dr. Gibbon succeeded in a first cardiac surgery with an artificial heart-lung machine. From that time, the safety of the cardiac surgery has been improved by various improvements in heart-lung machines and development of myocardial depressants. Now, the use of extracorporeal circulation makes-it possible to perform the cardiac surgery safely.

However, even at the present state of the art, the cardiac surgeries with the heart-lung machines are at risk for the following postoperative complications:
(1) Complication in the brain: Cerebral hypoxemia or cerebral edema resulting from incorrect perfusion. Cerebral infarction due to embolization by of tissue fragments into the blood caused by interfusion of intake-air into extracorporeal circulation in the heart-lung machine or by operation to connect the heart-lung machine to the patient.
(2) Complication in the lung: hypoxemia or ventilatory insufficiency caused by various inflammentory substances, which are activated by the heart-lung machine.
(3) Renal dysfunction: Acute renal failure caused by decrease in renal blood flow due to use of the heart-lung machine.
(4) Blood cell injuries: Blood cell injuries are taken place by performing perfusion of the blood into the artificial, i.e., heart-lung machine. This may cause renal dysfunction, resulting in necessity of blood infusion.
(5) Postoperative bleeding: Postoperative bleeding may occur by the disorder of the in-vivo hemostatic function caused by the heart-lung machine.
(6) Aortic dissection: By insertion of an arterial inflow cannula into the aorta, the endothelium of the blood vessel may be injured and induced the acute aortic dissection. This complication is extremely serious condition and death rate of a patient is high.
(7) Other complications: Postperative infective diseases and multiple organ failure caused by decrease of immunologic reaction.

It is often the case that these complications cause systemic inflammation even if the patient's condition is not severe and the length of postoperative stay in the hospital takes one week at the least. Further, the artificial circulation passages used in operation is of disposable, a high medical cost presents problems for the patients.

Recently, a tendency to avoid the side effects due to use of the artificial hear-lung is seen in the field of coronary artery bypass, and operations without use of the artificial hear-lung machine have been popularized. In particularly, minimally invasive surgery employing an endoscope is widely used and has become of major interest lately because of low occurence of complications and rapid recovery after operation.

Even in the field of cardiac surgery, there is an increasing demand for intracardiac surgeries which can be performed without use of any hear-lung machine. It is however, impossible to stop the beat of the heart. Further, it is pointed out that there would be considerable difficulty in use of the endoscope since the blood and beating heart obstructs the view from the endoscope.

Commercially available catheter devices such as "Amplatzer" (brand name), "Angelwing" (brand name) are applied for treatment of atrial septal defects. These devices are designed for uniformly distributed defects as targets. Thus, it is difficult with such devices to treat the intracardiac defects since these defects vary with the individual patient. For these reasons, there is a great demand for any breakthrough for realizing cardiac surgery without use of any artificial heart-lung machine.

SUMMARY OF THE INVENTION

It is therefore an object of the present invention to provide an intracardiac suture device for performing minimally invasive cardiac surgery on intracardiac defects without use of any artificial heart-lung system.

The present invention has been made on the basis of a method of introducing a suture device into the heart of a patient through a sheath after surgically incising the chest region of a patent.

According to the present invention, there is provided an intracardiac suture device, comprising:

a first shaft assembly comprising a first shaft having a lumen passing therethrough from a proximal end to a distal end thereof, a first suture needle-holding means coaxially provided at and spaced from the distal end of the first shaft, and a connector with a hemostatic valve provided on the proximal end of the first shaft;

a second shaft assembly comprising a second shaft having a lumen passing therethrough from a proximal end to a distal end thereof and being slidably arranged in the first shaft assembly, and a connector with a hemostatic valve and provided on the proximal end of the second shaft;

a third shaft assembly comprising a hollow third shaft slidably arranged in the second shaft assembly, and handling portion provided at a proximal end of the third shaft; and a puncture assembly comprising a hollow operating rod provided at a proximal end thereof, and a second suture needle-holding means provided at a distal end thereof and removably arranged in the distal end of the third shaft, said hollow operating rod being connected to the proximal end of the second suture needle-holding means and movably arranged in the third shaft assembly;

wherein said second shaft is protrusible by sliding-movement from the distal end of the first shaft toward the first suture needle-holding means, and wherein a suture needle is transferable between the first suture needle-holding means and the second suture needle-holding means when the third shaft is slid to the distal end of the second shaft after sliding the second shaft to a position where a suture site is held between the second shaft and the first suture needle-holding means.

In one embodiment of the present invention, the second suture needle-holding means comprises a flexible hollow member with an inner diameter slightly larger than an outer diameter of a suture needle, and the hollow member is provided with an enlarged head portion having a proximal end thereof with an outer diameter smaller than the inner diameter of the third shaft, and a distal end with an outer diameter larger than the inner diameter of the third shaft. The enlarged head portion includes a portion tapered toward the proximal end thereof. The hollow member is provided with plural slits at the distal portion thereof including said enlarged head portion, so that the enlarged head portion is reduced in inner diameter thereof to hold the suture needle when the enlarged head portion is received in the third shaft. In this case, the third shaft is preferably provided with an annular rib at a distal portion of the lumen thereof so that the enlarged head portion is prevented from movement toward the proximal end thereof when the enlarged head portion is housed in the third shaft.

Further, the hollow member may be provided at a proximal end thereof with a flange and a coil spring arranged around the hollow member and between the flange and the annular rib, so that the operating rod is automatically moved backward by the restoring force of the coil spring, which has been compressed by forward movement of the operation rod.

In order to improve the operationality of the second suture needle-holding means, the operating rod may be provided at a proximal end thereof with a handling portion, which is adapted to be moved forward and backward with respect to the handling portion of the third shaft assembly.

In one embodiment of the present invention, the first suture needle-holding means comprises a flexible hollow member having a needle-holding portion with an inner diameter slightly smaller than the suture needle. The hollow member is provided at an end of the first shaft side or a distal end thereof with a needle loading port and at the distal side thereof with plural longitudinally extending slits.

In another embodiment of the present invention, the first suture needle-holding means comprises a flexible hollow member having a needle-holding portion with an inner diameter slightly smaller than the suture needle and including an enlarged head portion provided at a distal end thereof, a hollow clamping member movably mounted on the hollow member to surround the enlarged head portion, and a coil spring arranged around the hollow member on the proximal end of the hollow member with respect to the clamping member. The hollow member is provided at the distal end side thereof with longitudinal slits. The clamping member is adapted to be moved between a first position where it compresses the hollow member, and a second position where it releases the hollow member from compression.

The intracardiac suture device may be provided with visual monitoring means for monitoring a position of the device in the heart. Further, the connector of the first or second shaft assembly may be provided with a side tube for infusion of heparin, a saline solution or the like.

The present invention will be explained below, making reference to the accompanying drawings, which show, by way of example only embodiments thereof.

DETAILED DESCRIPTION OF THE INVENTION

Figure 1:
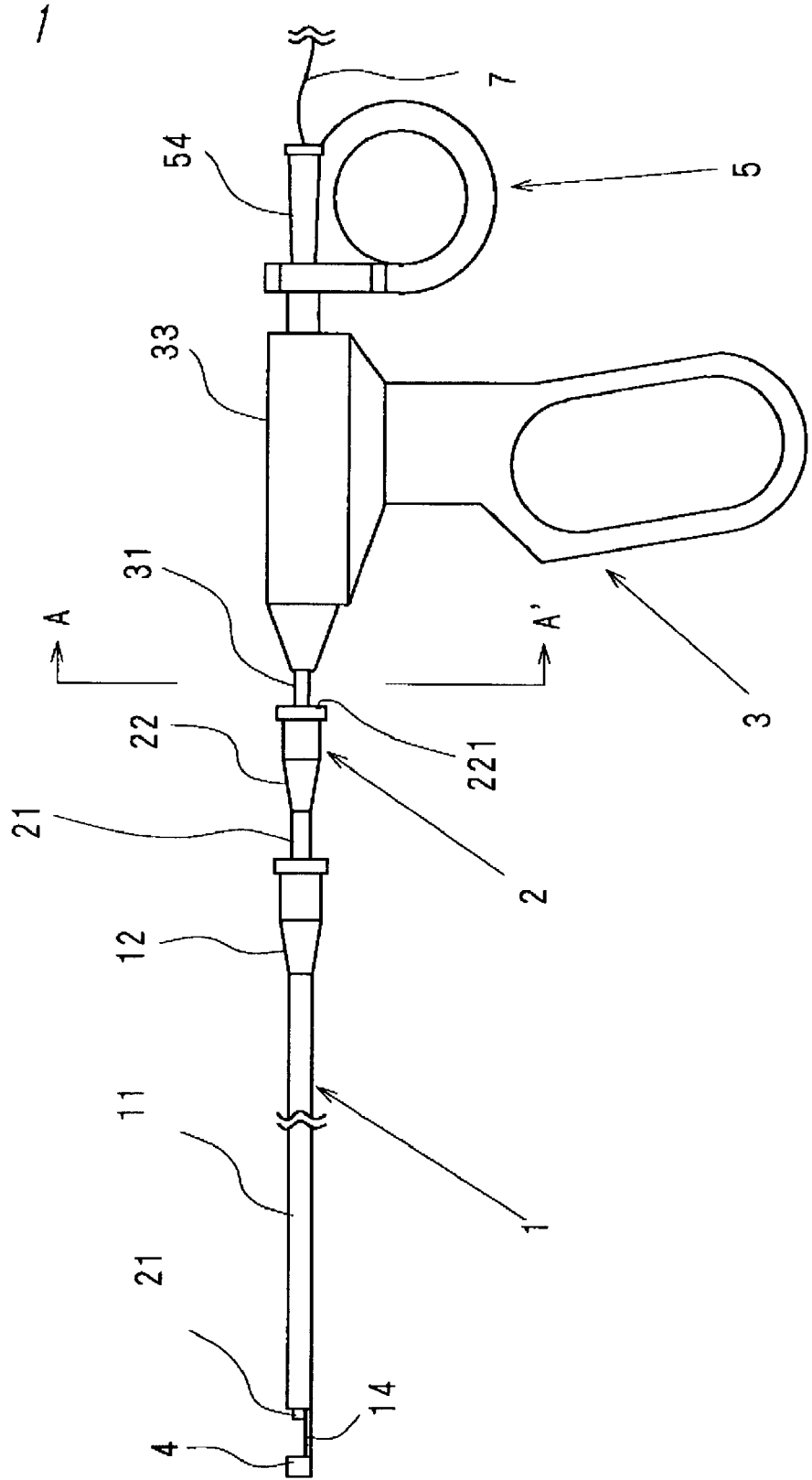
FIG. 1 is a plane view illustrating one embodiment of an intracardiac suture device according to the present invention.

Referring now to FIGS. 1 to 7, there is shown an intracardiac suture device according to the present invention, which comprises:

a first shaft assembly 1 comprising a first shaft 11 and a first suture needle-holding means 4 provided at a distal end of the first shaft 11;

a second shaft assembly 2 comprising a second shaft 21 slidably arranged in the first shaft assembly 1;

a third shaft assembly 3 comprising a hollow third shaft 31 slidably arranged in the second shaft assembly 2 and a handling portion 33 provided at a proximal end of the third shaft 31; and a puncture assembly 5 provided at a proximal end thereof with a second suture needle-holding means 51, said second suture needle-holding means 51 being removalbly arranged in the distal end of the third shaft 31;

wherein said second shaft 21 is protrusible by sliding-movement from the distal end of the first shaft 11 toward the first suture needle-holding means 4, and wherein a suture needle 6 is transferable between the first suture needle-holding means 4 and the second suture needle-holding means 51 when the third shaft 31 is slid to the distal end of the second shaft 21 after sliding the second shaft 21 to a position where a suture site is held between the second shaft 21 and the first suture needle-holding means 4.

Figure 6:
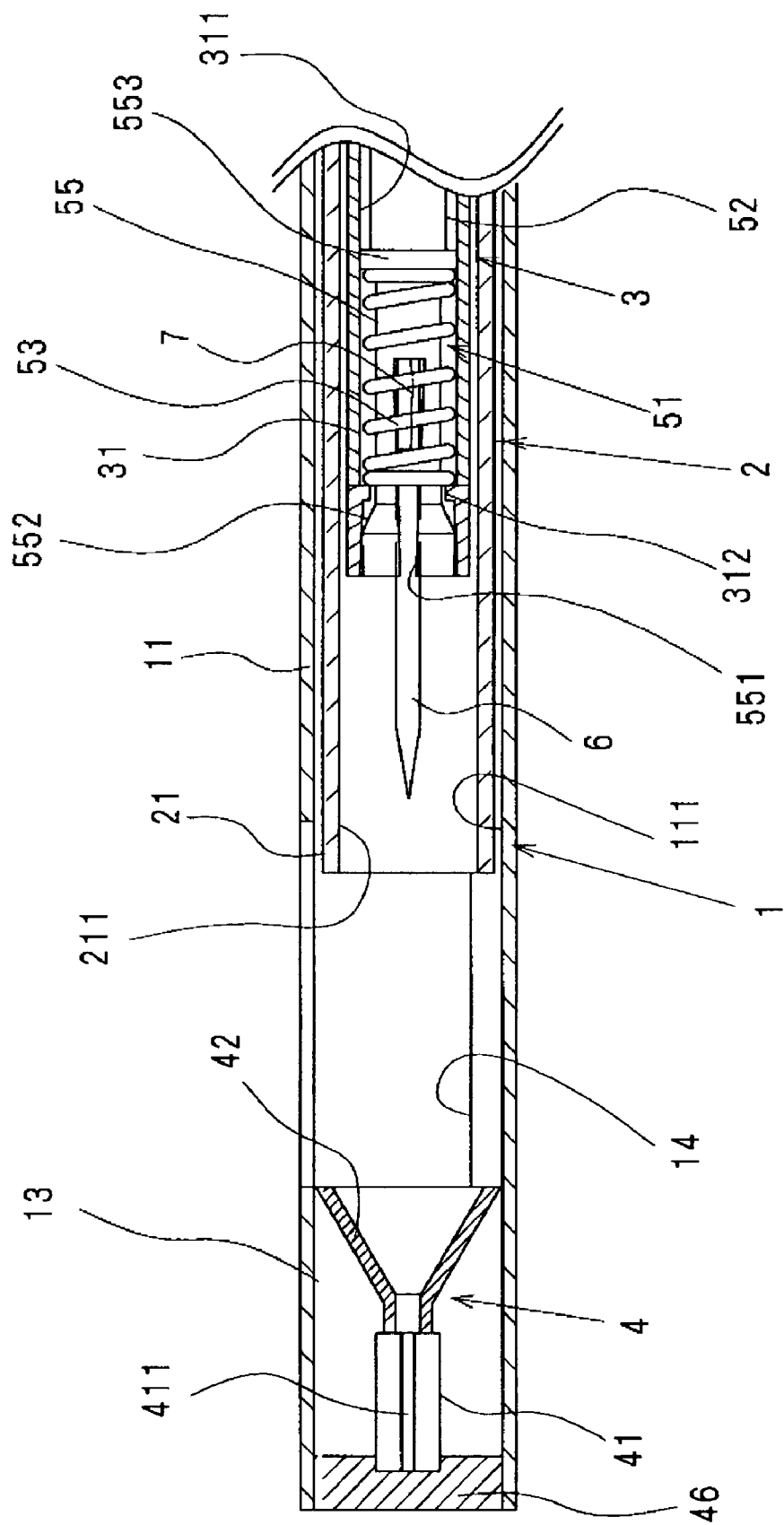
FIG. 6 is a longitudinal sectional view illustrating the distal end of the suture device of FIG. 1, which includes first and second suture needle holding portions.
Figure 7:
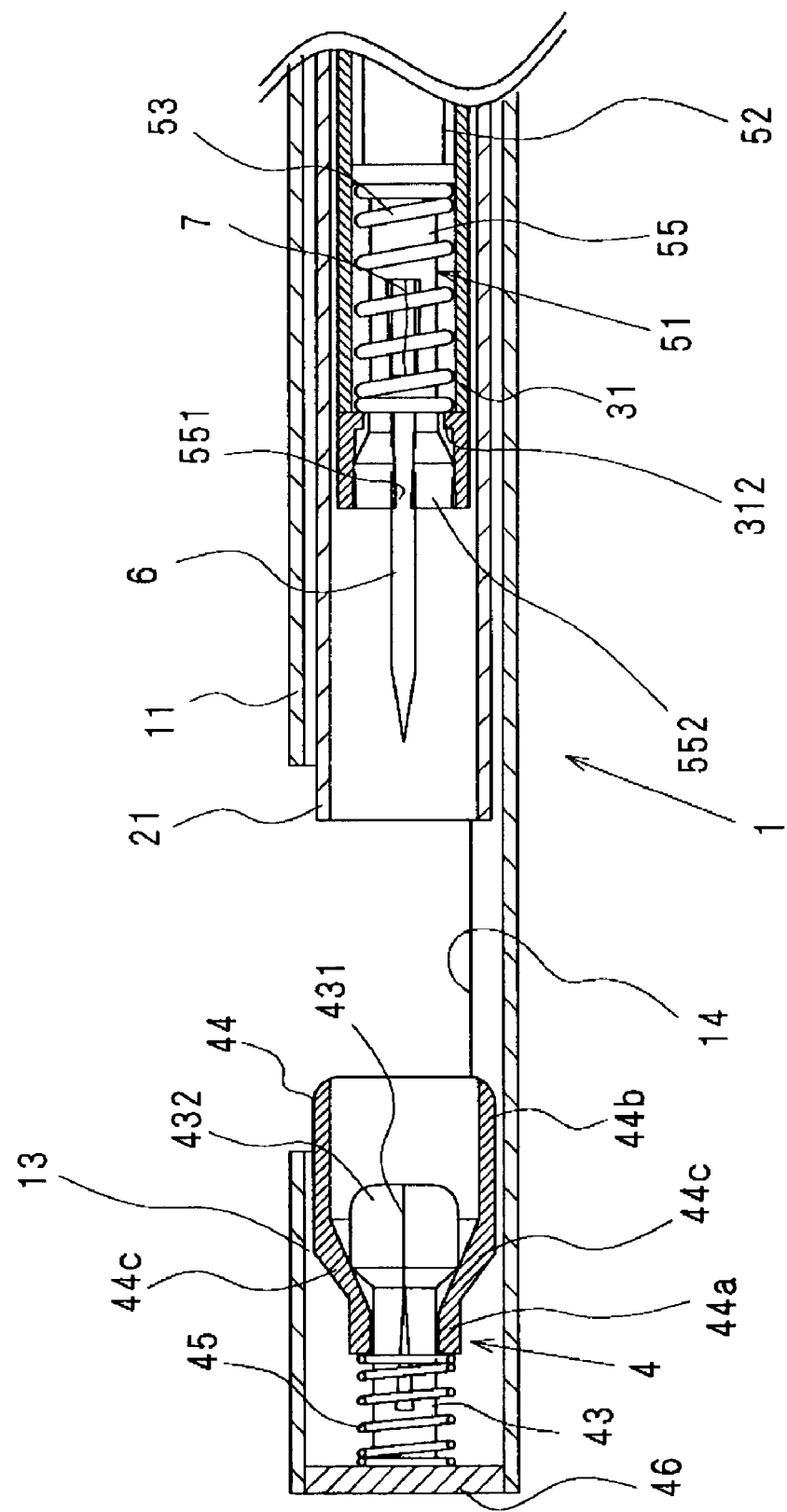
FIG. 7 is a longitudinal sectional view illustrating another embodiment of the distal end of the suture device of FIG. 1, which includes the first suture needle holding portion.

As illustrated in FIGS. 6 and 7, the first shaft assembly 1 comprises a first shaft 11 having a lumen 111 passing therethrough from a proximal end thereof to a distal end thereof; a first suture needle-holding means 4 coaxially provided at and spaced from the distal end of the first shaft 11; and a connector 12 with a hemostatic valve provided on the proximal end of the first shaft 11.

The first shaft 11 is a tubular member made of a metal such as stainless steel, brass, meshed or coiled stainless steel, or a synthetic resin such as fluororesin(e.g., polytetrafluoroethylene), polypropylene, polyethylene, polyamide, polyethylene terephthalate, polyurethane. Into the lumen 111 passing through the first shaft 11 from the distal end thereof to the proximal end thereof, the second shaft assembly 2 (in fact, the second shaft 21) is slidably inserted through the connector 12 provided on the proximal end of the first shaft 11.

The connector 12 is a tubular member generally made of a synthetic resin such as polypropylene, ABS (acrylonitrile-butadiene-styrene) resin, polyvinyl chloride, polyethylene and polyethylene terephthalate, or a metal such as stainless steel, brass and the like. The connector 12 is provided at the proximal end thereof with a port 121 for insertion of the second shaft 21, and in an interior thereof with a hemostatic means (not illustrated in the drawings) for preventing leakage of the blood during operation.

Figure 2:
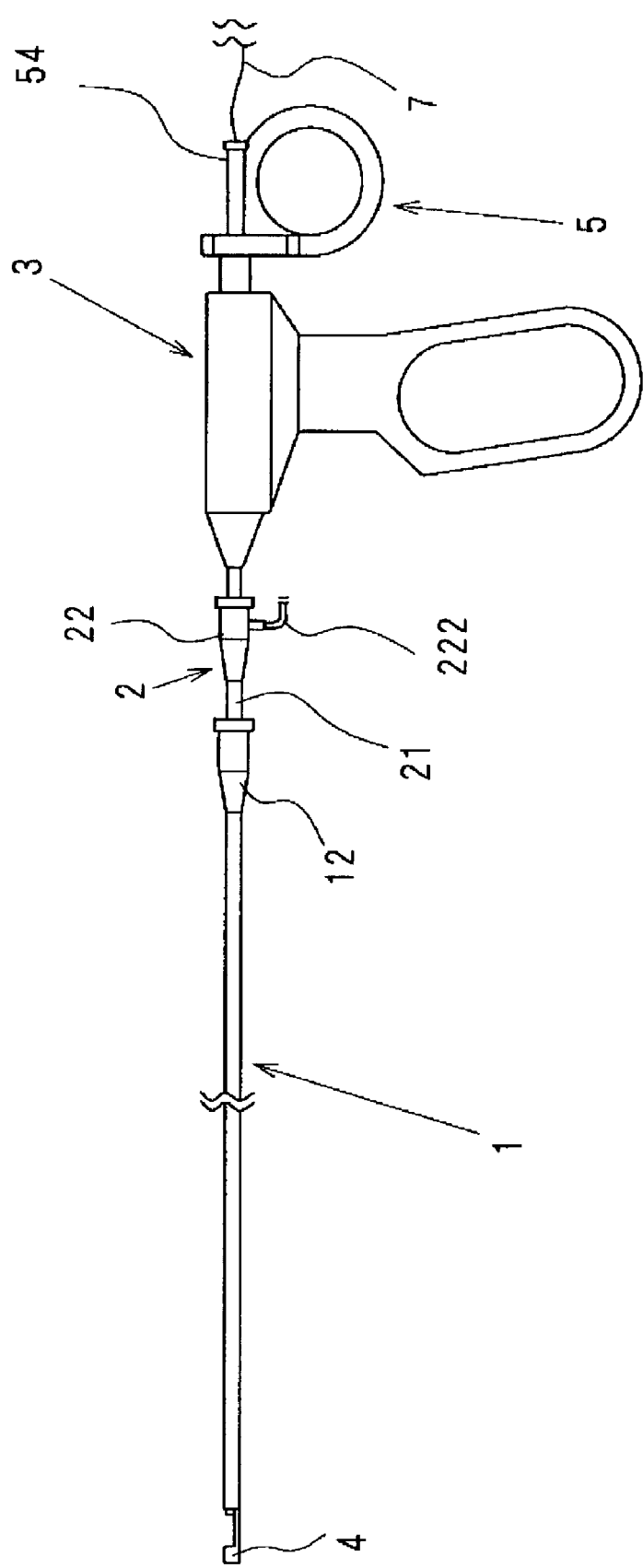
FIG. 2 is a plane view illustrating another embodiment of an intracardiac suture device according to the present invention.
Figure 3:
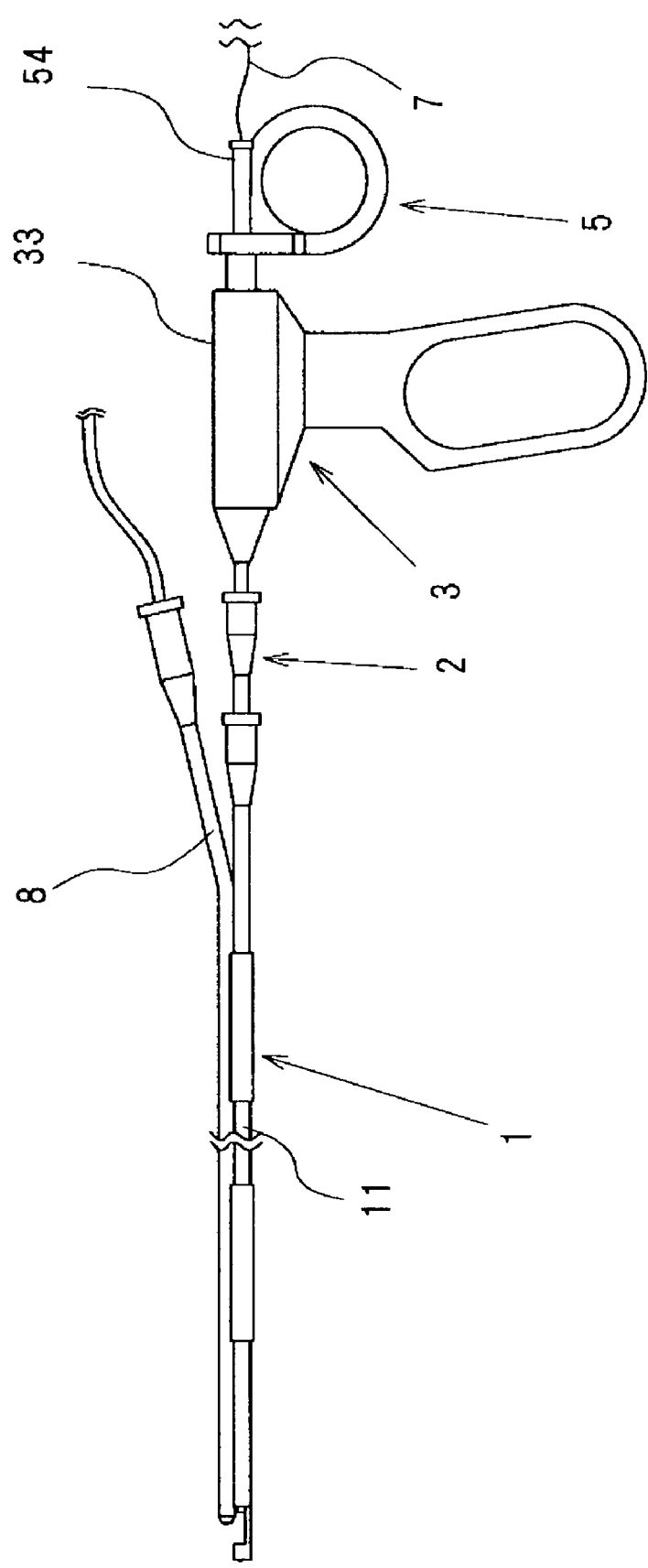
FIG. 3 is a plane view illustrating another embodiments of an intracardiac suture device according to the present invention.
Figure 4:
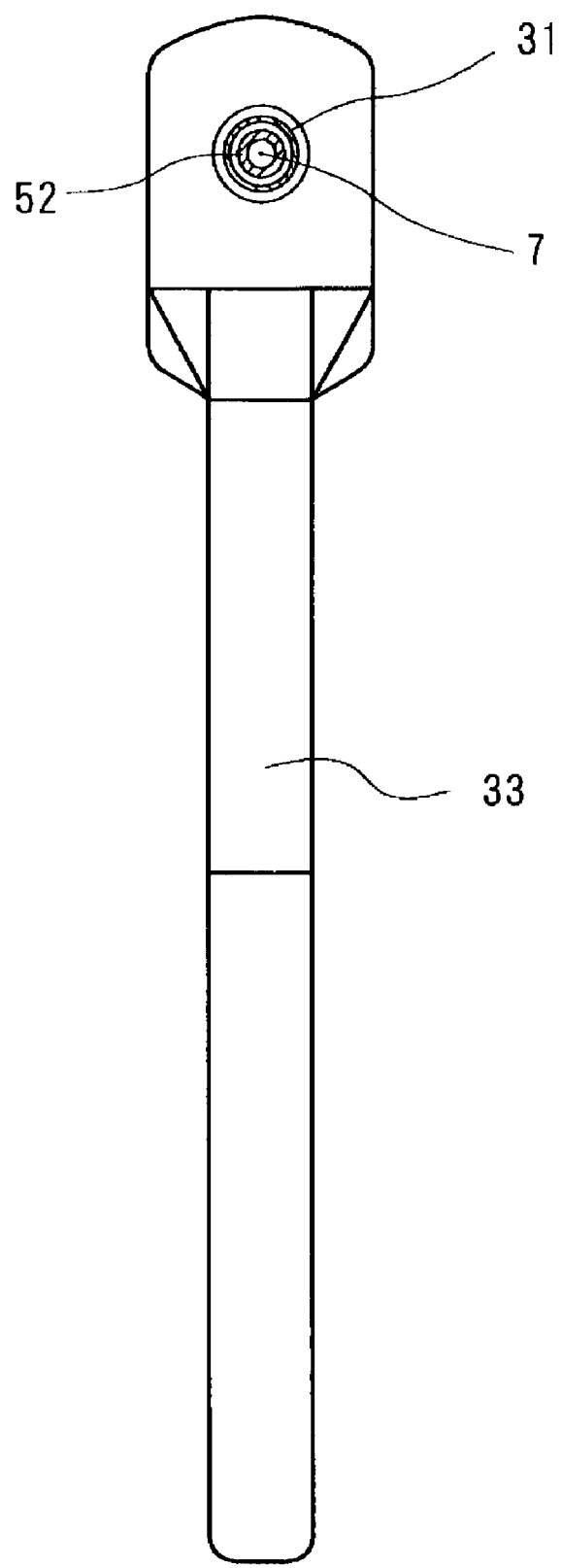
FIG. 4 is a sectional view illustrating the suture device of FIG. 1 taken along a line A–A'.

The first suture needle-holding means 4 may be housed in a gripper holding portion 13, which is formed as an integral part of a tube forming the first shaft 11. In this case, as shown in FIGS. 1 to 3, the tube forming the first shaft 11 is provided at a distal end thereof with the gripper holding portion 13 spaced by a notch 14 formed between the holding portion 13 and the distal end of the first shaft 11. The notch 14 has a predetermined length and a depth sufficiently greater than a radius of the first shaft 11. The gripper holding portion 13 is closed at the distal end thereof by a closing member 46 to which the first suture needle-holding means 4 is fixed.

The first suture needle-holding means 4 is arranged in the gripper holding portion 13 such that the distal end thereof is directed to the first shaft 11. The first suture needle-holding means (or a first suture needle gripper) 4 may be comprised of, as shown in FIG. 6, a flexible hollow member 41 having a needle-holding portion with an inner diameter slightly smaller than the suture needle 6, and a needle loading port 42 provided on a distal end of said flexible hollow member 41. The hollow member 41 is provided with plural slits 411 extending in the longitudinal direction thereof.

Alternatively, the first suture needle-holding means 4 may be a suture needle-holding assembly as illustrated in FIG. 7.

The suture needle-holding assembly 4 comprises a flexible slit hollow member 43 having a needle-holding portion with an inner diameter slightly smaller than the suture needle 6 and including an enlarged head portion 432 provided at a distal end thereof, a hollow clamping member 44 movably mounted on the hollow member 43 to surround the enlarged head portion 432, and a coil spring 45 arranged around the hollow member 43 on the side of the proximal end of the hollow member 43 beyond the clamping member 44. The above hollow member 43 is provided at a distal end thereof with an enlarged head portion 432, and fixed at the distal end thereof to a closure member 46. The hollow member 43 is provided with plural longitudinal slits 431 at the distal end side of hollow member 43 including the enlarged head portion 432. The clamping member 44 is a stepped hollow cylindrical member including a small-sized proximal portion 44a, a large-sized distal portion 44b surrounding the enlarged head portion 432 of the hollow member 43, and a middle portion 44c having an inner diameter tapered from the distal portion to the proximal portion. The large-sized distal portion of the clamping member 44 has an inner diameter greater than the outer diameter of the enlarged head portion 432 but slightly smaller than the inner diameter of the gripper holding-portion 13, which is then tapered toward the small-sized proximal portion of the clamping member 44. The small-sized proximal portion of the clamping member 44 has an inner diameter slightly larger than the outer diameter of the proximal end of the hollow member 43. The clamping member 44 is housed in the gripper holding portion 13 together with the hollow member 43. The coil spring 45 is located between the closing member 46 and clamping member 44 to force the clamping member 44 toward the distal end of the hollow member 43. The clamping member 44 is movable between a first position (or an initial position) where it compresses the hollow member 43, and a second position where it releases the hollow member 43 from compression (i.e., a position where an outer wall of the enlarged head portion 432 is free from contact with an inner wall of the clamping member 44 as the clamping member 44 is moved toward the distal end of the gripper holding portion 13 under compression of the coil spring 45).

The hollow members 41 and 43 of the fist suture needle-holding means 4 may be made of the material such as metals including stainless steel, brass and the like; and flexible resins including polypropylene, polyethylene, polyamide and the like. The needle loading port 42 may be made of materials such as synthetic resins including fluororesin (e.g., polytetrafluoroethylene), polypropylene, polyethylene, polyamide, polyethylene terephthalate, polyurethane and the like. The clamping member 44 may be made of the same materials as those used for the hollow members 41 and 43.

As illustrated in FIGS. 6 and 7, the second shaft assembly 2 comprises a slender second shaft 21 having a lumen 211 passing therethrough from a distal end thereof to a proximal end thereof; and a connector attached to the proximal end of the second shaft 21 and having a hemostatic valve provided therein. The second shaft 21 is adapted to be slidably moved toward the first suture needle-holding means 4. The second shaft 21 is a slender hollow tubular member and made of the same material as that used for the first shaft 11. The lumen 211 extending from the proximal end to the distal end of the second shaft 21 is adapted to receive a third shaft assembly 3 (in fact, a third shaft 31) inserted through the connector 22.

The connector 22 is a tubular member made of the same material as that of the connector 12, and is provided at a proximal end thereof with a port 221 for loading the third shaft 311 thereinto. The connector 22 includes a hemostatic means provided therein (not illustrated in the drawings) for preventing the blood from leakage during operation.

The third shaft assembly 3 comprises a hollow third shaft 31, and a handling portion 33 attached to a proximal end of the third shaft 31. The third shaft 31 is a slender tubular member made of the same material as that of the first shaft 11 and having a lumen 311 passing therethrough from a distal end thereof to a proximal end thereof. The third shaft 31 is provided at the proximal end thereof with the handling portion 33 for actuating it back and forth by sliding movement, through which an operating rod 52 of a after-mentioned second suture needle-holding means 51 is inserted movably back and forth. There is no limit to a material for the handling portion 33, but the handling portion 33 is generally made of the same as that used for the third shaft 31.

The puncture assembly 5 is slidably arranged in the third shaft assembly 3. The puncture assembly 5 comprises a slender hollow operating rod 52 having a distal end and a proximal end and provided at the distal end thereof with a second suture needle-holding means 51. The second suture needle-holding means 51 is positioned in the distal end of the third shaft 31 and adapted to be put in and out the lumen 311 of the third shaft 31. The operating rod 52 is movably arranged in the lumen 311 of the third shaft 31.

The second suture needle-holding means 51 comprises a flexible hollow member 55 having an inner diameter slightly larger than the diameter of the suture needle 6 and an outer diameter smaller than the inner diameter of the third shaft 31. The hollow member 55 is provided at the distal end thereof with an enlarged head portion 552, which is extended from the hollow member 55, reversely tapered toward the distal end thereof and reached to a uniform outer diameter greater than the inner diameter of the third shaft 31. The hollow member 55 is provided with plural slits 551 longitudinally extending from the distal end of the enlarged head portion 552 towards the proximal end of hollow member 55.

The hollow member 55 is fixed at the proximal end thereof to the hollow operating rod 52 slidably arranged in the lumen 311 of the third shaft 31. The enlarged head portion 552 is adapted to hold the suture needle 6 therein by reduction of the inner diameter thereof when the enlarged head portion 552 is housed in the third shaft 31. In this case, as illustrated in FIGS. 6 and 7, the third shaft 31 is preferably provided with an annular rib 312 at the distal portion of the lumen 311 thereof to prevent the enlarged head portion 552 from movement toward the proximal thereof at the time of seating of the enlarged head portion 552 in the third shaft 31.

When the enlarged head portion 552 is pushed out of the lumen of the third shaft 31, the enlarged head portion 552 may be return to the lumen of the third shaft 31 by manually operating the operating rod 52. Alternately, the enlarged head portion 552 may be returned automatically to its original position by providing an auto-return mechanism, which comprises, for example, a flange 553 provided at the proximal end of the hollow member 55, and a coil spring 53 arranged around the hollow member 55 and between the flange 553 and the annular rib 312 so that the coil spring 53 is compressed when the operating rod 52 is pushed forward in the third shaft 31, and then restored by the restoring force of the coil spring 53 to automatically house the enlarged head portion 552 to the lumen 311 of the third shaft 31, as illustrated in FIGS. 6 and 7.

Further, in order to improve the operationality of the second suture needle-holding means 51, the operating rod 52 may be provided at a proximal end thereof with a handling portion 54, which is adapted to be moved forward and backward with respect to the handling portion 33 of the third shaft assembly 3.

In the suture device comprised of the first, second and third shaft assemblies 1, 2, 3 and the puncture assembly 5, the suture needle 6 is transferred between the first suture needle-holding means 4 and the second suture needle-holding means 51 when the third shaft 31 is moved to the distal end of the second shaft 21 that had been moved beyond the distal end of the first shaft 1 to a position where a suture site is held between the second shaft 21 and the first suture needle-holding means 4.

As illustrated in FIG. 3, the intracardiac suture device of the present invention may be provided with a visual monitoring means such as an endoscope 8, a ultrasound probe (not illustrated in the drawings) or the like, to check the position of the suture device in the heart. Further, as illustrated in FIG. 2, the connector 12 of the first shaft assembly 1 or the connector 22 of the second shaft assembly 2 may be provided with a side tube 222 for infusion of heparin, saline for irrigation and the like.

The hollow member 55 of the second suture needle-holding means 51 may be made of, without being limited to, the same materials as those used for the hollow member 43 of the first suture needle-holding means 4 as the hollow member 55 has the same structure and function as those of the hollow member 43 of the first suture needle-holding means 4.

Using the intracardiac suture device of the present invention, closure of defects may be carried out in the manner mentioned below with reference to FIGS. 8 to 15.

Figure 5:
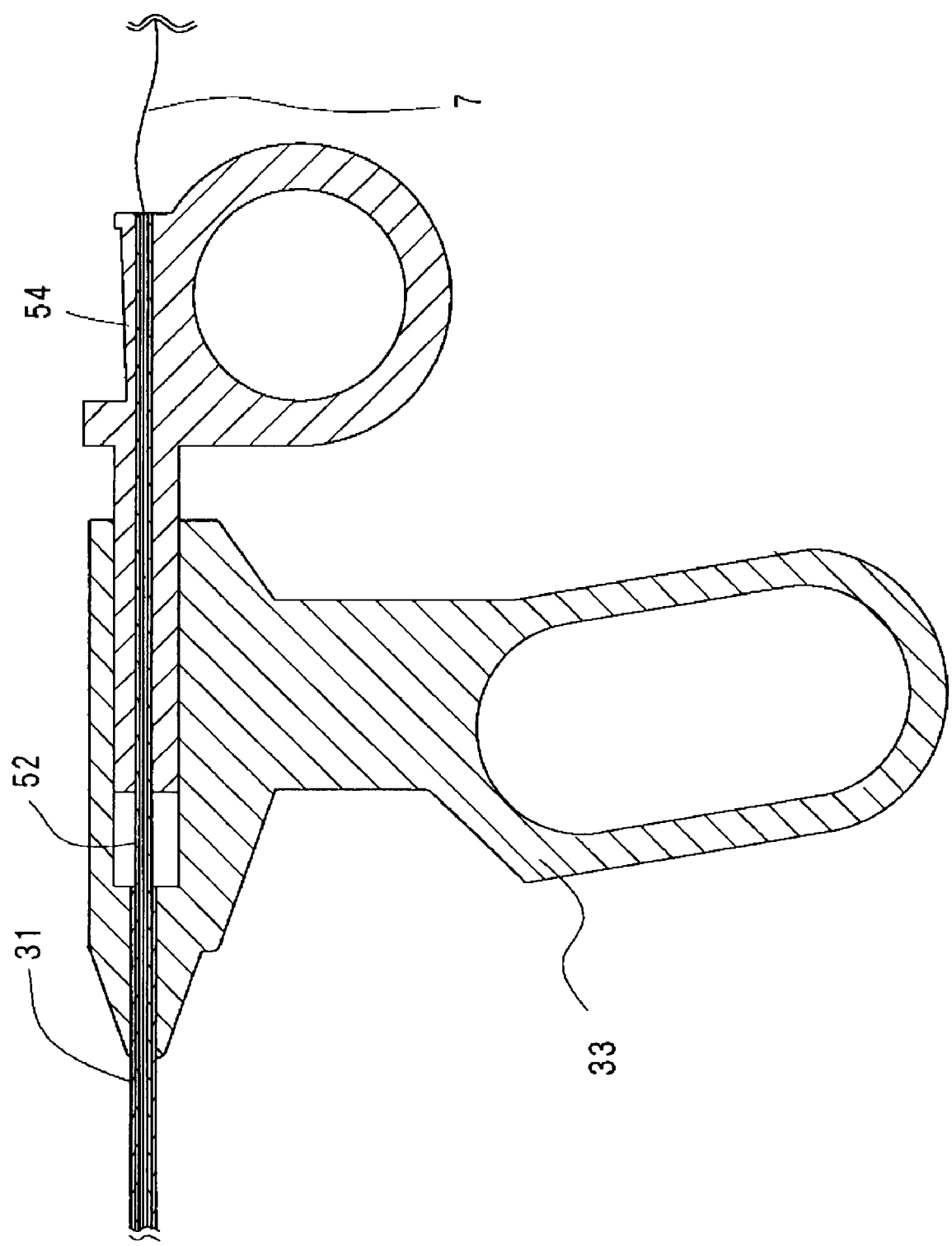
FIG. 5 is a longitudinal sectional view illustrating the proximal end of the suture device of FIG. 1.

Firstly, the heart is exposed by surgical incision of the chest of a patient and punctured at an appropriate part of the heart (usually, the right auricle). A sheath (not illustrated in the drawings) for insertion of an intracardiac suture device is inserted near a suture site through the punctured part. Then, the intracardiac suture device as illustrated in FIG. 1 is inserted into the sheath until the distal end thereof reaches to the position near the suture site. Before insertion, the suture device is set so as to have a positional relationship as illustrated in FIGS. 5 and 6 between the third shaft 31 and the second suture needle-holding means 51.

Figure 8:
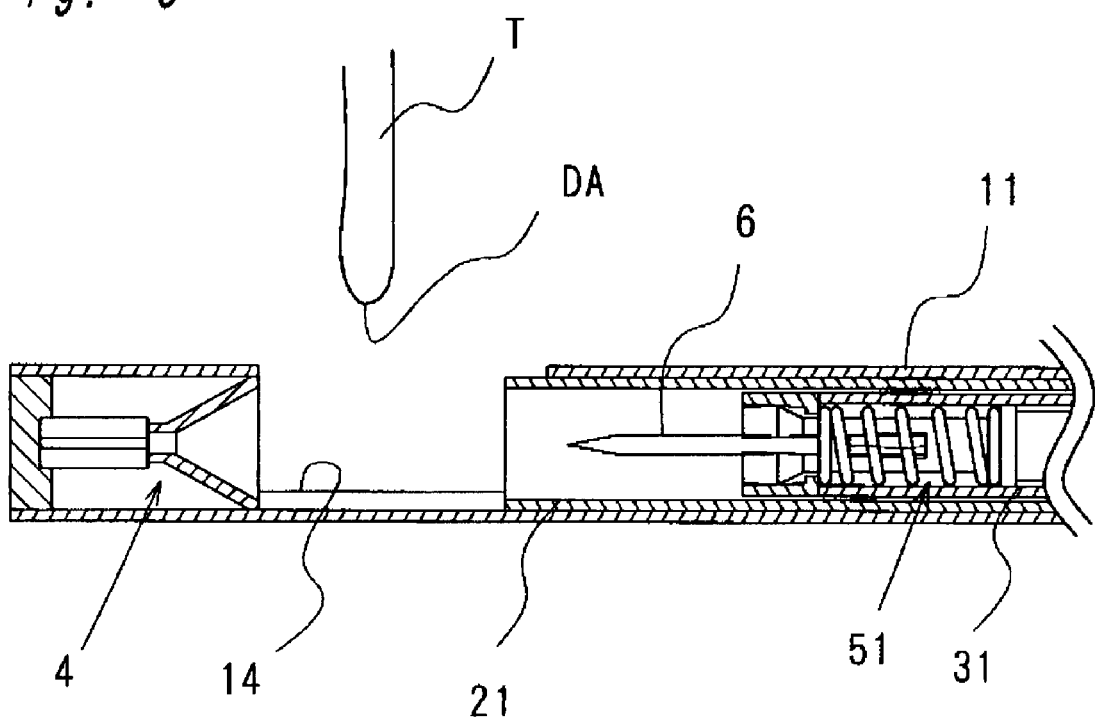
FIGS. 8 to 15 are schematic diagrams illustrating suture operation using the intracardiac suture device of the present invention.
Figure 9:
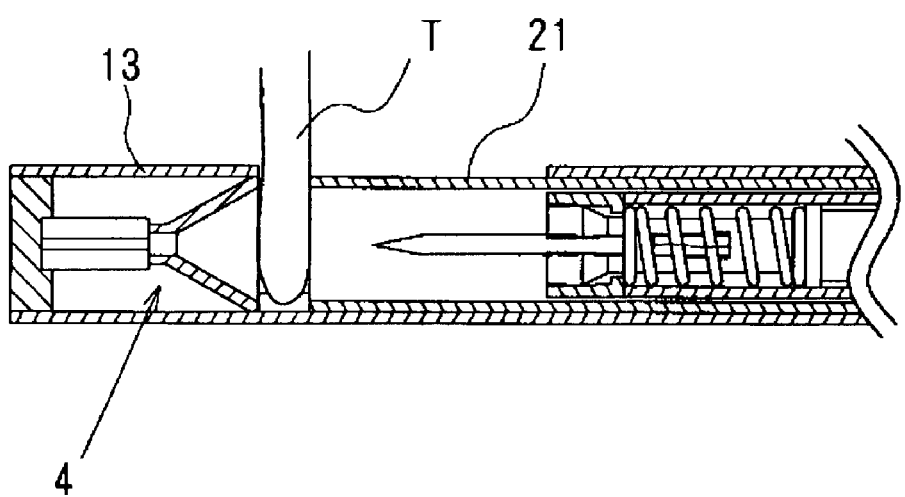
Figure 10:
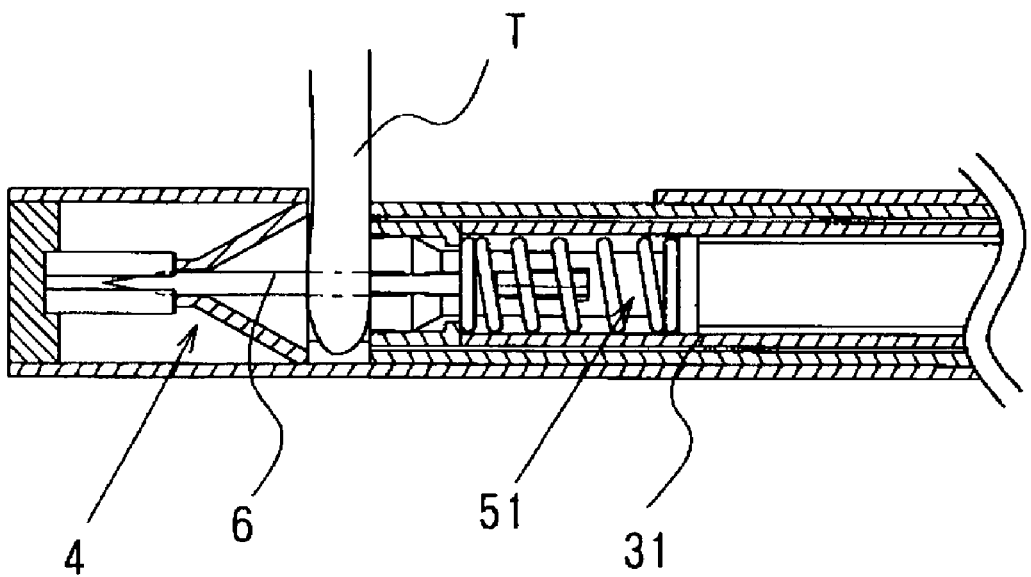
Figure 11:
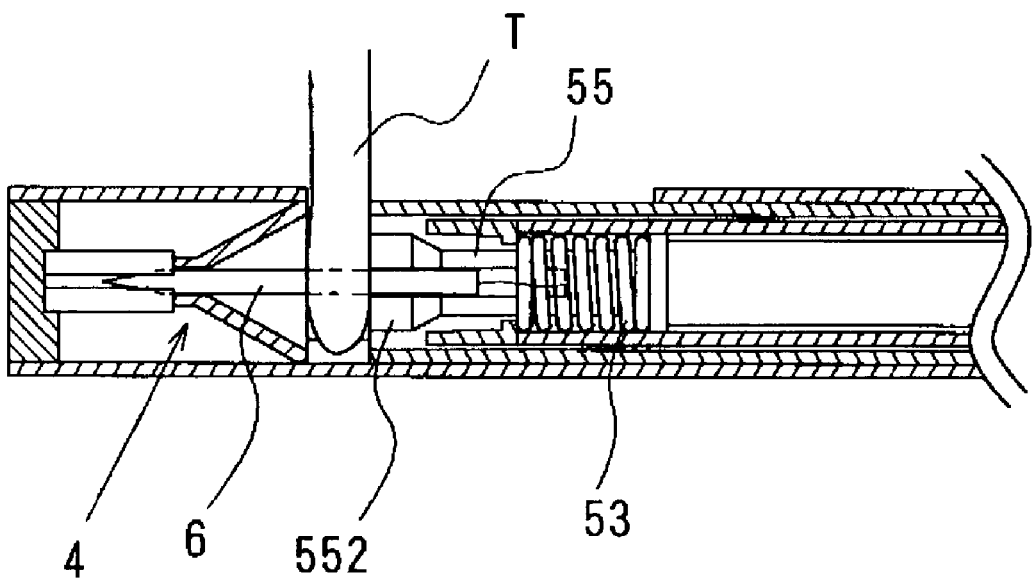

As illustrated in FIG. 8, the distal end of the suture device is protruded from the sheath to locate the first suture needle-holding means 4 within a defect aperture DA of the heart so that the notch 14 is located in the defect aperture. The second shaft assembly 2 is pushed manually over the first shaft assembly 1 to hold a tissue T surrounding the defect aperture DA between the distal end of the second shaft 21 and the gripper holding portion 13. If necessary, this procedure may be carried out with checking out the relationship between the device and the suture site in the heart with the visual means such as the endoscope 8. At that time, the third shaft assembly 3 moves forward along with the second shaft assembly 2 (cf. FIG. 9). At a state where the tissue T is held between the gripper holding portion 13 and the second shaft 21, when the handling portion 33 is pushed manually over the second shaft assembly 2 and thereby the third shaft assembly 3 is pushed forward to the second shaft assembly 21 with the result that the second puncture needle holding means 51 is moved forward along with the third shaft 31. Thus, the puncture needle 6 held by the second puncture needle holding means 51 in the third shaft 31 is moved forward to puncture the tissue T, inserted into the first suture needle-holding means 4 and received therein at the distal end thereof (cf. FIG. 10).

Figure 12:
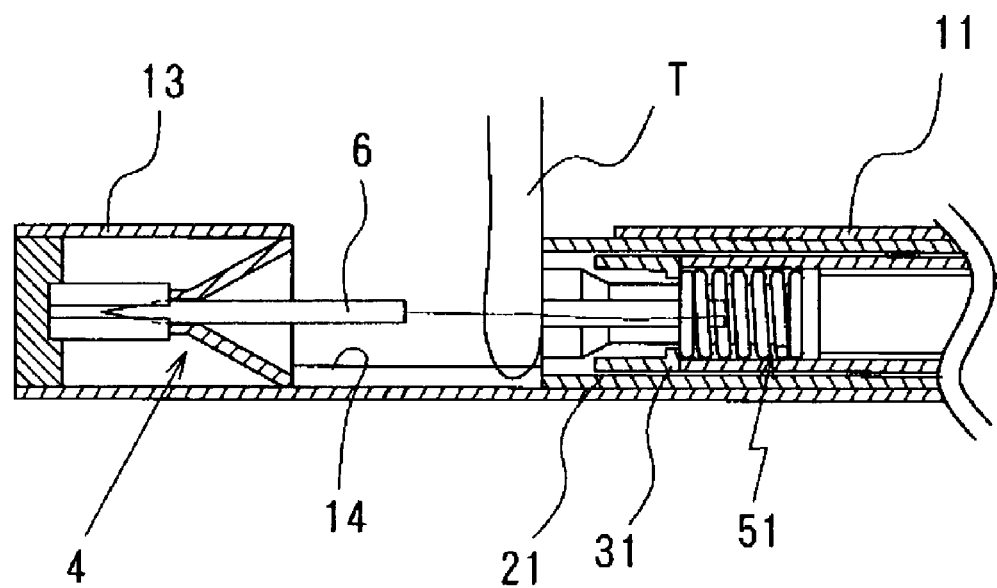

Then, by retreating the handling portion 33 toward the handling portion 54 of the puncture assembly 5, the enlarged head portion 552 is unsheathed from the third shaft 31 and thus the hollow member 55 is released from the compression pressure of the third shaft 31. Thus, the hollow member 55 is returned to the uncompressed condition where the inner diameter of the hollow member 55 is larger than the outer diameter of the suture needle 6, and the suture needle 6 is released from the second suture needle-holding means 51 (cf. FIG. 11). At the same time, the backward movement of the handling portion 33 compresses the coil spring 53. Under the condition illustrated in FIG. 11, the first shaft assembly 1 is manually pushed forward over the second shaft assembly 2 as it stands, with the result that the suture needle 6 is moved forward along with the first suture needle-holding means 4, passed through the tissue T, and transferred to the first suture needle-holding means 4 on the opposite side of the second suture needle-holding means 51 with respect to the tissue T, as illustrated in FIG. 12.

Figure 13:
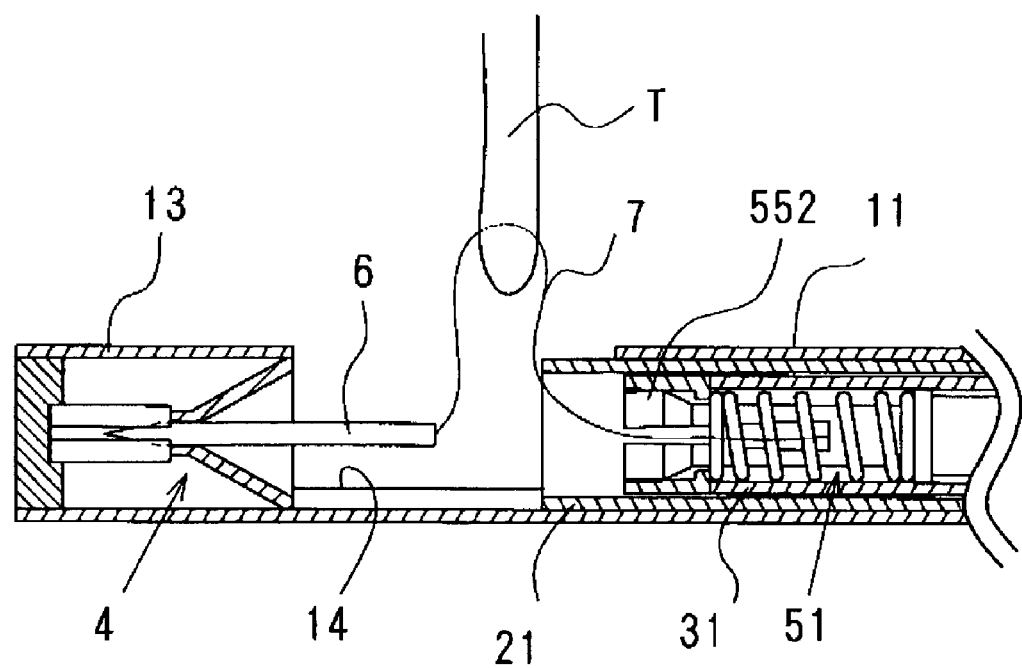
Figure 14:
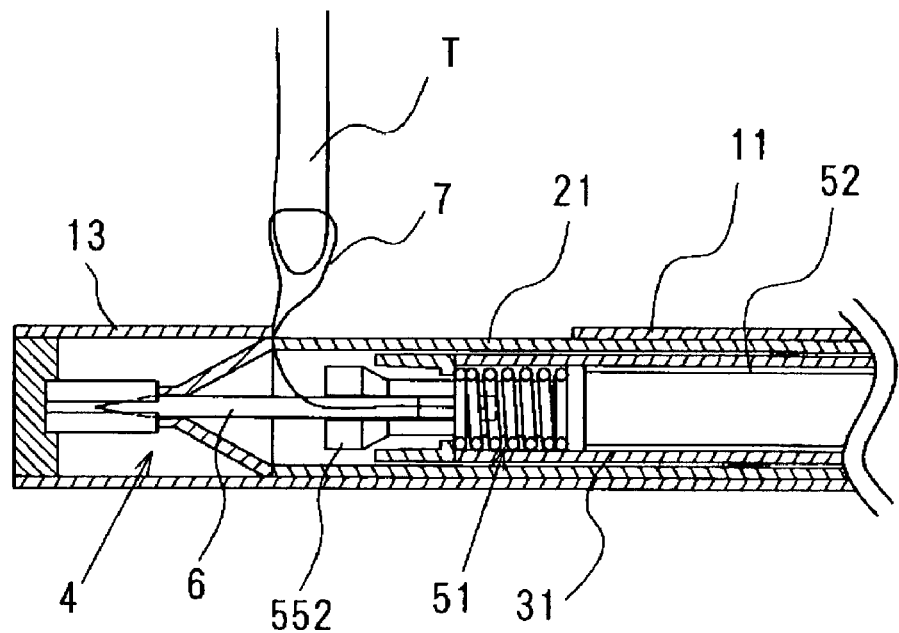

The whole suture device is moved backward to a certain extent and the handling portion 54 of the puncture assembly 5 is taken off while holding the handling portion 33 as it stands. And then the second suture needle holding means 51 is moved backward by the restoring force of the coil spring 53 and the enlarged head portion 552 is pulled in the lumen 311 of the third shaft 31. The tissue T is brought out from the notched portion 14 by manipulating the whole of the suture device, as illustrated in FIG. 13. Under the conditions of FIG. 13, the second shaft assembly 2 is pushed manually forward to the position near the distal end of the first shaft assembly 1, which is the same position as that illustrated in FIG. 9, and then the handling portion 33 is moved backward to the handling portion 54 of the puncture assembly 5, so that the enlarged head portion 552 is unsheathed from the third shaft 31 and the hollow member 55 is released from the compression pressure of the third shaft 31. Thus, the hollow member 55 is returned to the uncompressed condition where the inner diameter of the hollow member 55 is larger than the outer diameter of, the suture needle 6. Under such a condition, by pushing the handling portion 33 to advance the third shaft assembly 3 over the second shaft assembly 2, the suture needle 6 is received by the second suture needle-holding means 51 as illustrated in FIG. 14. At that time, the coil spring 6 is being compressed.

Figure 15:
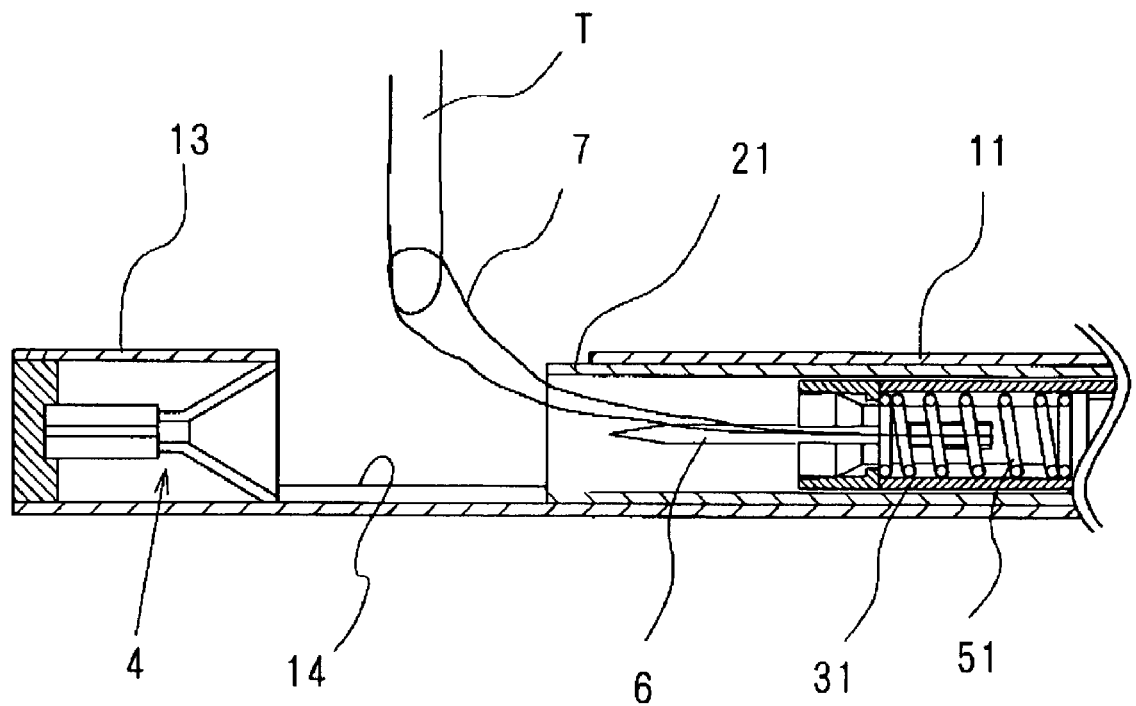

Then, by losing hold of the handling portion 33 while holding the second shaft assembly 2 and the handling portion 54 of the puncture assembly 5, the third shaft assembly 3 is moved forward by the restoring force of the coil spring 53. For this reason, the enlarged head portion 552 is received in the third shaft 31 and the hollow member 55 is compressed by the third shaft 31 to make the inner diameter of the hollow member 55 smaller than the outer diameter of the suture needle 6, so that the suture needle 6 is held by the suture needle holding means 51. Under such a condition, when the first shaft assembly 1 is pushed forward to move it over the second shaft assembly 2, the suture needle 6 is transferred to the second suture needle holding means 51 and brought to the condition as illustrated in FIG. 15.

The closure of defect is completed by repeating the above procedures several times, and carrying out ligature and cutting of the suture with a special purpose device.

As will be understood from the above description, the use of the intracardiac suture device of the present invention makes it possible to perform a minimally invasive operation for suturing intracardiac defects without use of any artificial heart-lung system.

Further, the present invention makes it possible to perform intracardiac operations certainly and safely at a lower cost as compared with the conventional operations using any artificial heart-lung system. In addition, the present invention makes it possible to minimize risk of complications after the operation since the recovery time after operation is reduced to about one day, which is very short as compared with the recovery time of more than one week. Also, the present device is easy to operate and contribute to reduce burdens for an operator.

What is claimed is:

1. An intracardiac suture device, comprising:
 a first shaft assembly comprising a first shaft having a lumen passing therethrough from a proximal end to a distal end thereof, a first suture needle-holding means coaxially provided at and spaced from the distal end of the first shaft, and a connector with a hemostatic valve provided on the proximal end of the first shaft;
 a second shaft assembly comprising a second shaft having a lumen passing therethrough from a proximal end to a distal end thereof and being slidably arranged in the first shaft assembly, and a connector with a hemostatic valve provided on the proximal end of the second shaft;
 a third shaft assembly comprising a hollow third shaft slidably arranged in the second shaft assembly, and handling portion provided at a proximal end of the third shaft; and
 a puncture assembly (5) comprising a hollow operating rod provided at a proximal end thereof, and a second suture needle-holding means provided at a distal end thereof and removably arranged in the distal end of the third shaft, said hollow operating rod being connected to the proximal end of the second suture needle-holding means and movably arranged in the third shaft assembly;
 wherein said second shaft is protrusible by sliding-movement from the distal end of the first shaft toward the first suture needle-holding means, and wherein a suture needle is transferable between the first suture needle-holding means and the second suture needle-holding means when the third shaft is slid to the distal end of the second shaft after sliding the second shaft to a position where a suture site is held between the second shaft and the first suture needle-holding means.

2. The intracardiac suture device according to claim 1, wherein the second suture needle-holding means comprises a flexible hollow member with an inner diameter slightly larger than an outer diameter of a suture needle, said hollow member being provided with an enlarged head portion having a proximal end with an outer diameter smaller than the inner diameter of the third shaft, and a distal end with an outer diameter larger than the inner diameter of the third shaft, wherein said enlarged head portion includes a portion tapered toward the proximal end thereof, and wherein said hollow member is provided with plural slits at the distal portion thereof including said enlarged head portion, so that the enlarged head portion is reduced in inner diameter thereof to hold the suture needle when the enlarged head portion is received in the third shaft.

3. The intracardiac suture device according to claim 2, wherein the third shaft is provided with an annular rib at a distal portion of the lumen thereof so that the enlarged head portion is prevented from movement toward the proximal end thereof when the enlarged head portion is housed in the third shaft.

4. The intracardiac suture device according to claim 3, further including a flange provided at a proximal end of the hollow member and a coil spring arranged around said hollow member and between the flange and the annular rib, wherein the operating rod, which has been moved forward by operation followed with compression of the coil spring, is automatically moved backward by the restoring force of the coil spring.

5. The intracardiac suture device according to claim 1, wherein the operating rod is provided at a proximal end thereof with a handling portion adapted to be movable forward and backward over the handling portion of the third shaft assembly.

6. The intracardiac suture device according to claim 1, wherein the first suture needle-holding means comprises a flexible hollow member having a needle-holding portion with an inner diameter slightly smaller than the suture needle, and a needle loading port provided at an end of the first shaft side or a distal end of said flexible hollow member, said hollow member being provided with plural slits extending in the longitudinal direction thereof.

7. The intracardiac suture device according to claim 1, wherein the first suture needle-holding means comprises a flexible hollow member having a needle-holding portion with an inner diameter slightly smaller than the suture needle and being provided at a distal end thereof with an enlarged head portion, a hollow clamping member movably mounted on the distal side of the hollow member and adapted to surround the enlarged head portion, and a coil spring arranged around the hollow member on the proximal side of said hollow member with respect to the clamping member, the hollow member (43) being provided at the distal end side thereof with longitudinal slits.

8. The intracardiac suture device according to claim 1, further including visual monitoring means for monitoring a position of the device in the heart.

9. The intracardiac suture device according to claim 6 or 7, wherein the connector of the first or second shaft assembly is provided with a side tube for infusion of heparin, a saline solution or the like.

* * * * *